United States Patent
Wolf et al.

(10) Patent No.: US 7,299,089 B2
(45) Date of Patent: Nov. 20, 2007

(54) METHODS, SYSTEMS, AND COMPUTER PROGRAM PRODUCTS FOR NEURAL CHANNEL SELECTION IN A MULTI-CHANNEL SYSTEM

(75) Inventors: Patrick D. Wolf, Durham, NC (US); Deborah S. Won, Chapel Hill, NC (US)

(73) Assignee: Duke University, Durham, NC (US)

( * ) Notice: Subject to any disclaimer, the term of this patent is extended or adjusted under 35 U.S.C. 154(b) by 355 days.

(21) Appl. No.: 10/922,752

(22) Filed: Aug. 20, 2004

(65) Prior Publication Data
US 2006/0041203 A1 Feb. 23, 2006

(51) Int. Cl.
*A61F 2/70* (2006.01)
*A61B 5/0476* (2006.01)
(52) U.S. Cl. ............... 600/545; 600/544; 623/25
(58) Field of Classification Search ............ 623/25
See application file for complete search history.

(56) References Cited

U.S. PATENT DOCUMENTS 4,610,259 A * 9/1986 Cohen et al. ............. 600/544
7,120,486 B2 * 10/2006 Leuthardt et al. ......... 600/545

* cited by examiner

*Primary Examiner*—Charles A. Marmor, II
*Assistant Examiner*—Patricia C Mallari
(74) *Attorney, Agent, or Firm*—Jenkins, Wilson, Taylor & Hunt, P.A.

(57) ABSTRACT

Methods, systems, and computer program products for transmitting neural signal information. Methods, systems, and computer programs products are disclosed for neural channel selection in a multi-channel system. A method according to one embodiment can include a step for receiving a plurality of neural signals on a first plurality of channels. The method can also include a step for calculating criterion variable value for the neural signal on each of the channels. In addition, the method can include a step for ranking the channels by the criterion variable value. The method can also include a step for calculating mutual information between a measured output and a total population activity for the first plurality of channels. Further, the method can include a step for determining a second plurality of channels that encodes a predetermined amount of the mutual information.

57 Claims, 6 Drawing Sheets

METHODS, SYSTEMS, AND COMPUTER PROGRAM PRODUCTS FOR NEURAL CHANNEL SELECTION IN A MULTI-CHANNEL SYSTEM

GRANT STATEMENT

The subject matter disclosed herein was supported by DARPA grant BAA01-42 and a National Science Foundation Graduate Research Fellowship Program grant. Thus, the Government has certain rights in the subject matter disclosed herein.

TECHNICAL FIELD

The subject matter disclosed herein relates generally to neural signal processing. Specifically, the subject matter disclosed herein relates to methods, systems, and computer program products for neural channel selection in a multi-channel system.

BACKGROUND ART

The human brain is an exceedingly complex processing system, which integrates continual streams of incoming sensory input data with stored memories, uses the input data and memories in complex decision processes at both conscious and unconscious levels and, on the basis of these processes, generates observable behaviors by activation of its motor or movement control pathways and the muscles which these innervate. The neurons of the nervous system propagate input data by generating characteristic electrical pulses called action potentials (APs), or neural spikes, that can travel along nerve fibers in the form of neural signals. A single neuron or a group of neurons represent and transmit information by firing sequences of APs in various temporal patterns. Information is carried in the AP arrival times and spike counts.

In certain cases of traumatic injury or neurological disease, the brain can be partially isolated from the periphery. Input data from certain senses are thus lost, at least for a portion of the body, as are many voluntary movements. Spinal cord injury is a well-known example of traumatic injury. With spinal cord injury, the pathways that link higher motor centers in the brain with the spinal cord and that are used for control of voluntary movements can be functionally transected at the site of the injury. As a result, the patient is paralyzed, and can no longer voluntarily activate muscles that are innervated by regions of the spinal cord below the level of the injury. Despite the injury to their long fibers, however, many of the cells in these higher brain regions that control voluntary movement will survive and can still be activated voluntarily to generate electric signals for controlling voluntary movement. By recording the electrical activities produced from these cells with implantable neural sensors (e.g., a microwire electrode array, a microwire, a magnetic field detector, chemical sensor, or other neural sensor), a decoding algorithm can be applied to interpret and reproduce the user's intended movements for the control of external prostheses, such as an assist robot or an artificial limb, or functional electrical stimulation of paralyzed muscles. Additionally, these generated signals can be used for control of computer operations such as the movement of a cursor on a computer display. Current equipment allows extracellular records of hundreds of cortical neurons in primate subjects to be acquired onto a plurality of neural channels and processed to make predictions of hand position during a target tracking task. These predicted motor outputs can be used to control a multi-jointed robotic limb.

Current devices for obtaining neural signals employ hundreds of neural sensors and neural signals to obtain predictions of the user's intended movements. Generally, it has been assumed to require as many neural signals as can be recorded that are distributed across different areas of the frontal and parietal cortices in order to obtain the best predictions. However, even using hundreds of neural signals that are currently recorded places a significant burden on neural signal acquisition and processing equipment. It is possible that different groups of neural signals carry redundant information. If this is the case, a subset of the neural signal population may provide as much information as the whole population for prediction purposes.

Accordingly, there exists a need for improved and more efficient methods, systems, and computer program products for neural channel selection in a multi-channel system.

SUMMARY

Methods, systems, and computer programs products are disclosed for neural channel selection in a multi-channel system. A method according to one embodiment can include a step for receiving a plurality of neural signals on a first plurality of channels. The method can also include a step for calculating criterion variable value for the neural signal on each of the channels. In addition, the method can include a step for ranking the channels by the criterion variable value. The method can also include a step for calculating mutual information between a measured output and a total population activity for the first plurality of channels. Further, the method can include a step for determining a second plurality of channels that encodes a predetermined amount of the mutual information. The second plurality of channels can be a subset of the first plurality of channels.

Some of the objects having been stated hereinabove, and which are achieved in whole or in part by the present subject matter, other objects will become evident as the description proceeds when taken in connection with the accompanying drawings as best described hereinbelow.

BRIEF DESCRIPTION OF THE DRAWINGS

Exemplary embodiments of the subject matter will now be explained with reference to the accompanying drawings, of which.

DETAILED DESCRIPTION OF THE INVENTION

I. Definitions

Figure 1:
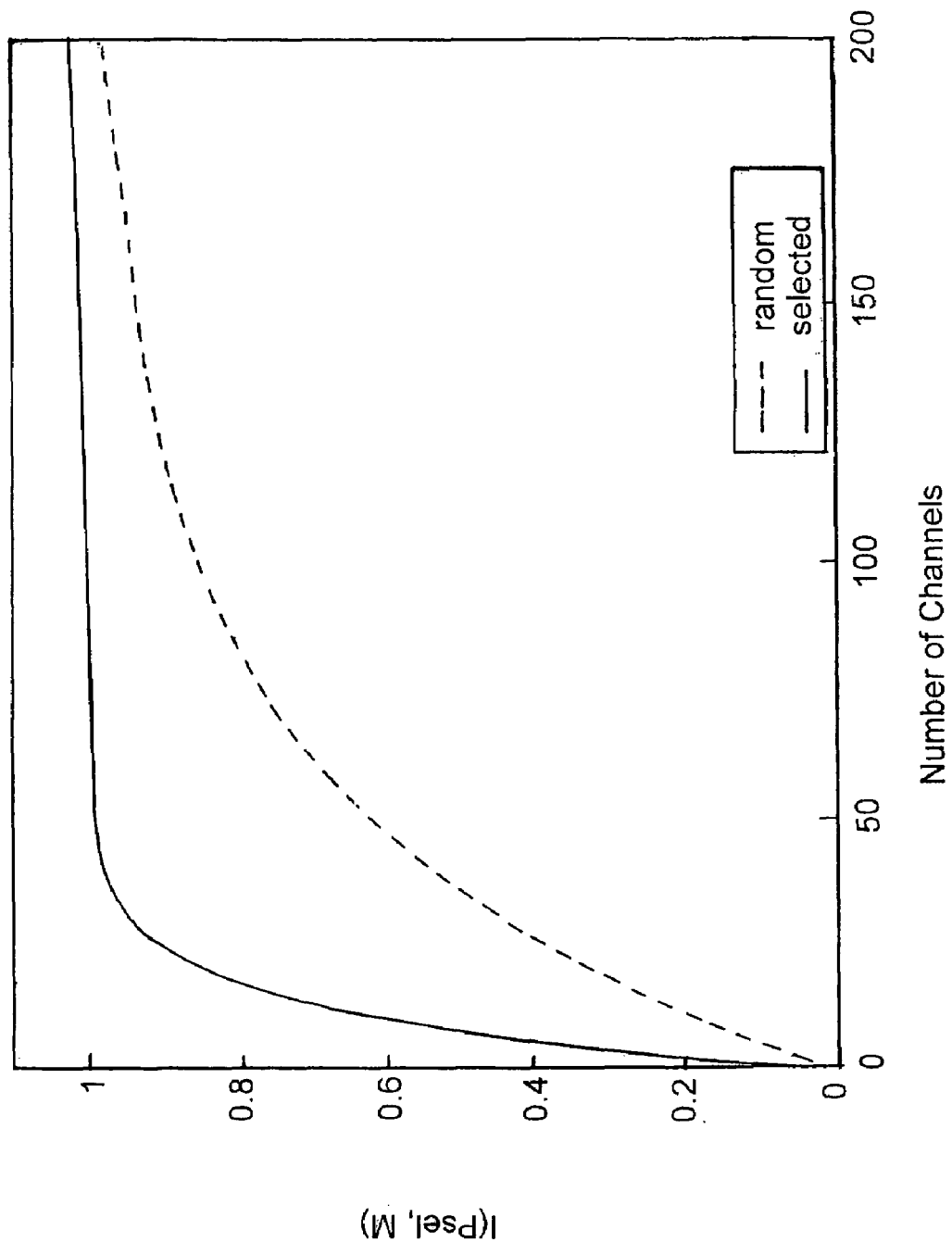
FIG. 1 is an exemplary graph showing hypothetical curves of channel population information versus channel population size.

Following long-standing patent law convention, the terms "a" and "an" mean "one or more" when used in this application, including the claims.

As used herein, the terms "action potential", "AP", and "neural spike" mean the characteristic electrical pulses that can travel along nerve fibers.

As used herein, the terms "actuator", "external device" and "prosthetic limb" are used interchangeably and mean any kind of device adapted to perform a movement or receive a command for controlling a system, such as a computer system. Although an actuator preferably performs a movement in three dimensions, an actuator can also be limited to performing movements in two dimensions. Thus, an actuator can be a manipulandum confined to two-dimensional motion. A representative actuator comprises a prosthetic limb, which can be fitted on, or integrated into, the body of a subject. An actuator can also be associated with machinery and/or circuitry that allow the actuator to respond to one or more forms of input with one or more movements. In one example, the range of motion of an actuator designated as a substitute for a patient's lost or paralyzed limb is limited to the range of motion of the limb for which the actuator is substituting.

As used herein, the term "location source" means a position wherein a neural sensor can detect one or more neural signals.

As used herein, the term "neural channel" means a medium operable to carry a representation of a neural signal recorded from a location source. For example, an electrical conduit is a medium capable of carrying an electrically-based representation of a neural signal.

As used herein, the term "neural signal" means a signal, which can take any form, originating in the nervous system of an organism. Neural signals typically include neural spike signals that carry information in their arrival times at destination neurons.

As used herein, the term "neural sensor" means an implantable device for sensing neural signals. Examples of neural sensors include microwire electrode arrays, optical sensors, microwires, magnetic field detectors, chemical sensors, and other suitable neural sensors which are known to those of skill in the art upon consideration of the present disclosure.

As used herein, the terms "operator," "patient" and "subject" are used interchangeably and mean any individual monitoring or employing the subject matter described herein, or an element thereof. Operators can be, for example, researchers gathering data from an individual, an individual who determines the parameters of operation of the present invention or the individual in or on which a high-density multichannel microelectrode array is disposed. Broadly, then, an "operator," "patient" or "subject" is one who is employing the present invention for any purpose. As used herein, the terms "operator," "patient" and "subject" need not refer exclusively to human beings, but rather the terms encompass all organisms having neural tissue, such as monkeys, dogs, cats, rodents, etc.

II. General Considerations

Through the years there has been significant research in the area of detecting and observing various electric potentials generated within the human body for medical diagnosis, biofeedback control of mental and physical states, and control of external devices. It is known that different regions of the brain are used to control different parts of the body and to process different sensory inputs. It is also known that when a human performs a certain function, such as moving an extremity or listening to a particular sound, multiple regions of the brain generate electrical action potentials to accomplish that function. It is also known that direct electrical stimulation of a particular region of the brain can reproduce, at least partially, the functions or sensory input normally associated with that region of the brain.

The methods, systems, and computer program products disclosed herein are operable to obtain neural signals on a plurality of neural channels for determining predictions of a user's intended movements. Hundreds of neural signals can be acquired simultaneously from neural sensors, conditioned, and processed to obtain predictions of the user's intended movements for the control of external devices. In one embodiment, 320 microwires are distributed across six different areas in the frontal and parietal cortices. The methods and systems disclosed herein can select channels to utilize the prediction algorithm. Utilizing neural signals on all channels is not necessary for accurately decoding hand position. A subset of the channel population can provide as much information as the whole channel population for accurate prediction purposes in a neural prothesis, actuator, or another external device. The methods and systems disclosed herein can determine a subset of the channel population for accurate prediction purposes.

It can be shown that a subset of the total neural channel population can attain prediction accuracy as measured by the coefficient of determination ($R^2$) that is comparable to or in some cases higher than using the entire neural channel population. For example, a linear prediction method can be applied to hand position in each of two dimensions and $R^2$ can be measured as groups of randomly selected channels are used to make predictions. FIG. 1 is an exemplary graph showing hypothetical curves of channel population information versus channel population size. The broken line represents the projected behavior of information as neural channels are randomly selected to be included in a subset channel population. The solid line represents the projected behavior of information as neural channels are added to a population in rank order of a criterion variable.

Figure 2:
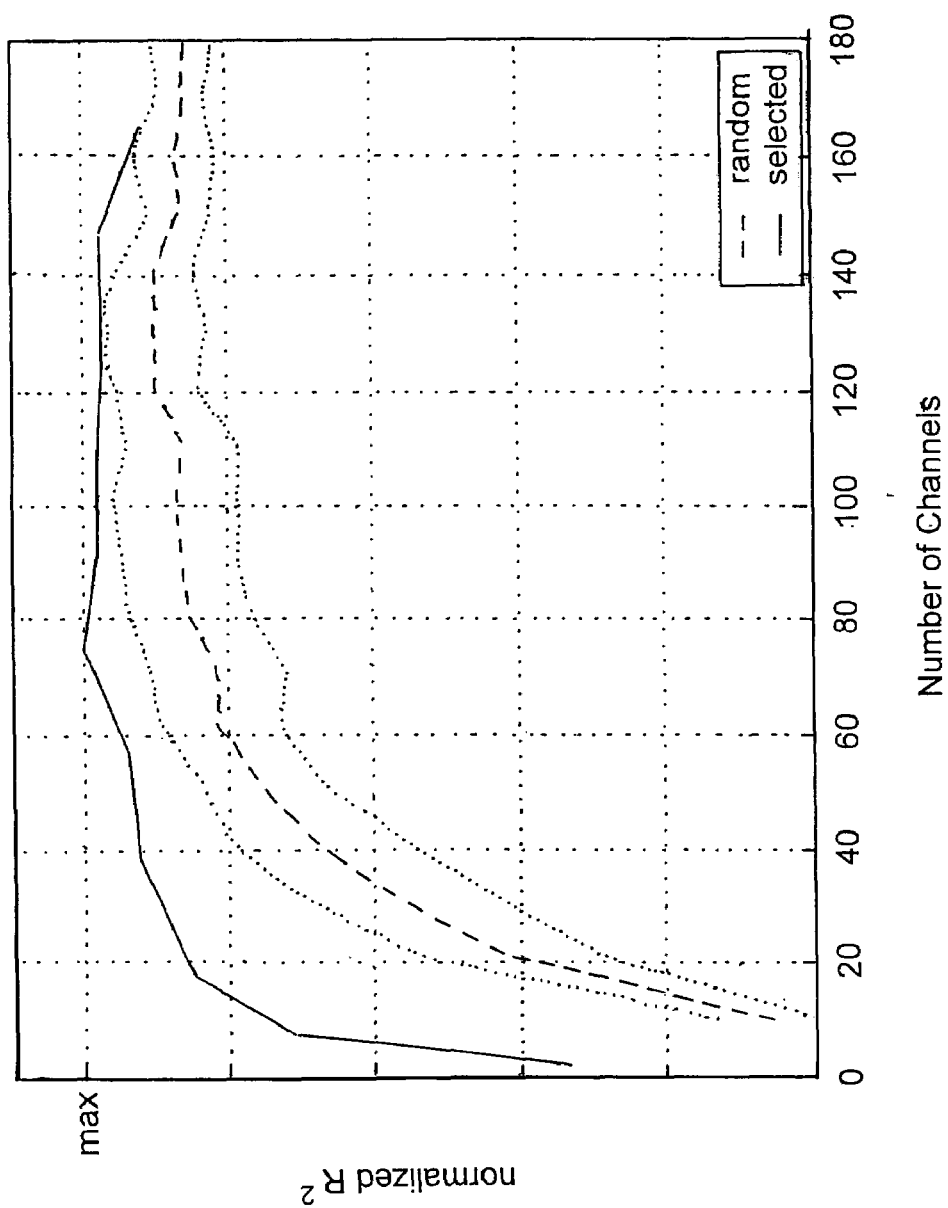
FIG. 2 is an exemplary graph showing experimental curves of $R^2$ for predictions of x position versus channel population size according to one embodiment.

FIG. 2 illustrates an exemplary graph showing experimental curves of $R^2$ for predictions of x position versus channel population size according to one embodiment. Analysis of the experimental results shown in FIG. 2 reveals that as the number of channels utilized increases, the coefficient of determination of hand position typically increases. However, random neuron dropping curves do not reveal as steep an increase in coefficient of determination as curves for selective channel populations do. Thus, FIG. 2 indicates that information can increase at a higher rate for smaller channel population sizes when channels are selectively included in the channel population in a selective order by rank order of a criterion variable rather than a random order.

III. Configuration and Operation of the Neural Channel Selection System

Methods, systems, and computer program products are disclosed herein for neural channel selection in a multichannel system. A subset of neural channels can be selected from a neural channel population to achieve suitable neural signals for processing. Initially, neural action potentials can be detected in signals received on a plurality of neural channels from neural tissues. The system can include neural sensors for detecting the neural signals on a plurality of neural channels. In addition, the system can include conditioning circuitry for conditioning the neural signals and a transmitter for transmitting the signals on each neural channel to a host station or computer for processing and storage. The host computer can implement a process to determine an optimal subset of the channels to enable or disable based on the neural signal information carried in the neural channels. The selected neural signals can be used in controlling an external device, such as an actuator, prosthetic device, or computer system, or to treat a neurological condition.

Enabling and disabling appropriate channels can improve efficiency in the transmission and processing of neural signals.

The methods, systems, and computer program products will be explained in the context of flow charts and diagrams. It is understood that the flow charts and diagrams can be implemented in hardware, software, or a combination of hardware and software. Thus, the subject matter disclosed herein can include computer program products comprising computer-executable instructions embodied in computer-readable media for performing the steps illustrated in each of the flow charts or implementing the devices illustrated in each of the diagrams.

III. A. Neural Channel Selection System

Figure 3:
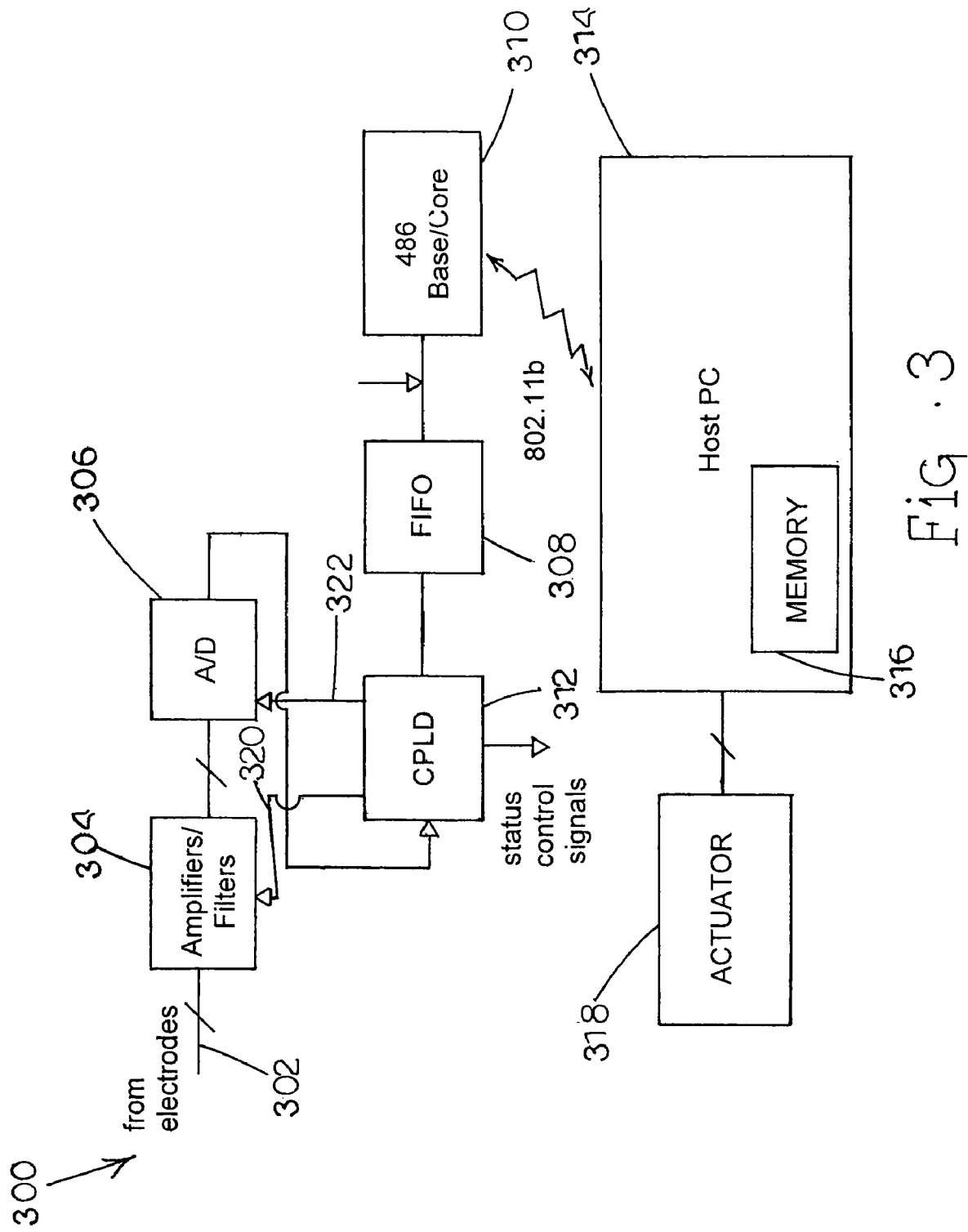
FIG. 3 is a schematic diagram of a neural channel selection system.

FIG. 3 is a schematic diagram of a neural channel selection system, generally designated 300, according to one embodiment. System 300 can include a plurality of microelectrodes 302 for detecting neural signals. Microelectrodes 302 can be implanted in different location sources in a subject's brain or nervous system. Neural signals detected on microelectrodes 302 can then be buffered, amplified, and filtered with amplifier and filtering circuitry 304. Selected channels can be serially digitized by an analog-to-digital (A/D) converter 306 and stored in a first-in first-out (FIFO) buffer 308 for wireless transmission through a radio frequency (RF) telemetry link 310. A complex programmable logic device (CPLD) 312 can control the timing and status of various operations through status signals sent to amplifying/filtering circuitry 304, A/D converter 306, and data transmission components 308 and 310.

The digitized data can be wirelessly transmitted to a host computer (or controller) 314 and stored in a memory 316. Host computer 314 can perform neural spike sorting on the multi-channel neural signals and apply signal processing to predict desired actuator position from the spike activity of the discriminated channels. The predicted position can be utilized to control the movements of an actuator 318. Thus, the neural signals can include data intended by the subject to control actuator 318. Actuator 318 can feedback its actual position to host computer 314.

Host computer 314 can also implement a selection process for selecting a subset of the channel population and indicating the selected channels to CPLD 312. CPLD 312 can then enable the selected subset of the channel population for conditioning and A/D conversion by circuitry 304 and A/D converter 306, respectively. CPLD 312 can indicate the selected subset of channels to enable by transmitting control signals to circuitry 304 and A/D converter 306 via control lines 320 and 322, respectively.

III. B. Neural Channel Selection Process

Figure 4:
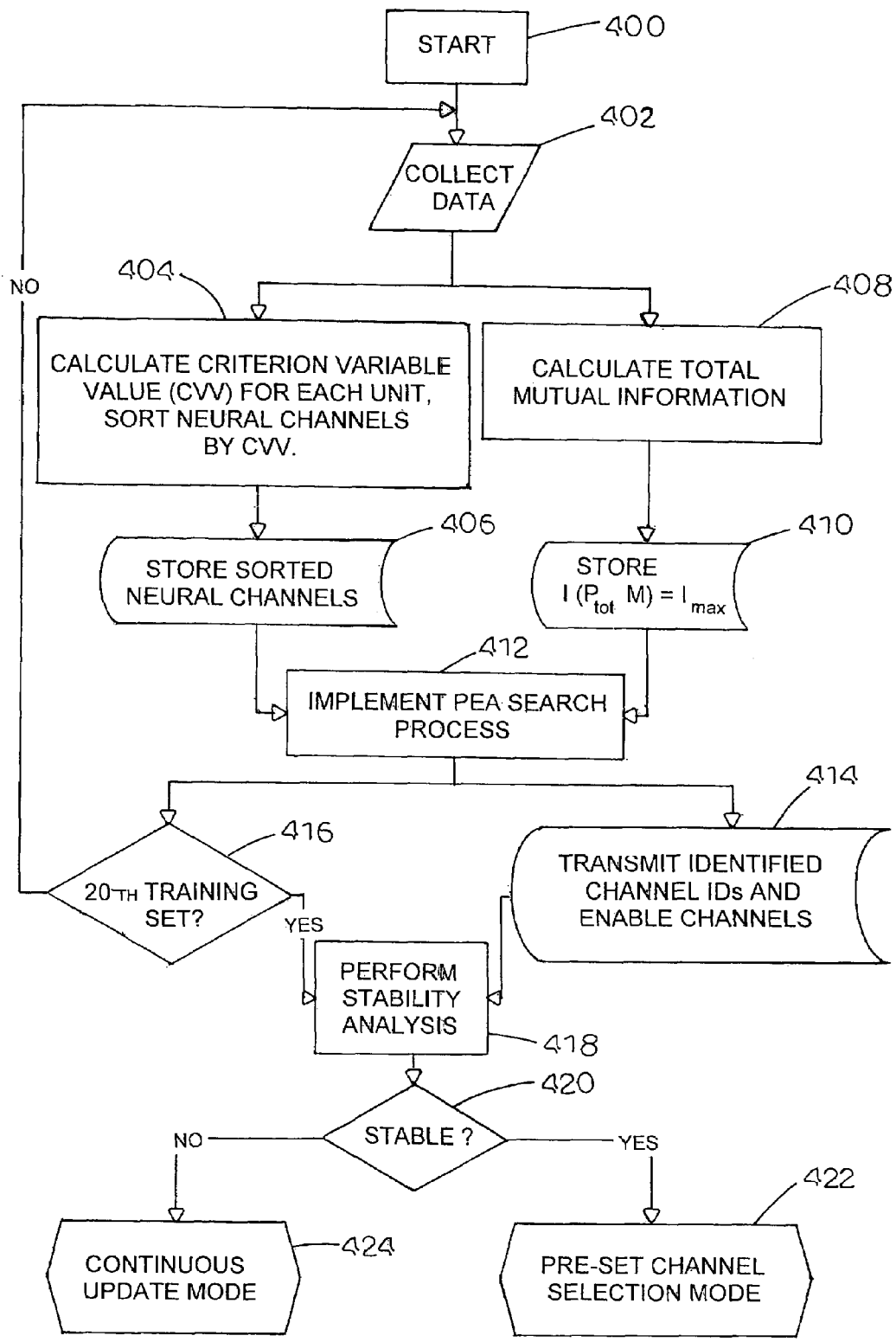
FIG. 4 is a flow chart illustrating an exemplary process for selecting neural channels in a multi-channel system.

FIG. 4 is a flow chart illustrating an exemplary process for selecting neural channels in a multi-channel system. The exemplary process of FIG. 4 is described with respect to system 300 (shown in FIG. 3) but can also be applied to various other suitable neural systems for selecting channels. Referring to FIG. 4, the process can start at step 400. Next, at step 402, system 300 can collect neural signals on a plurality of channels and output data from actuator 318 (FIG. 3). The neural signals can contain neural activity information and can be acquired from all available neural sensors 302. The number of neural channels can range on the order of hundreds to thousands. The data can be collected for a time period between approximately 2 and 10 minutes. The neural signals can include neural population activity (designated P for equations provided herein) such as temporal sequences of spike occurrences, spike counts over relatively long bins, or interspike intervals.

Neural signal collection can include detecting the neural signals with microelectrodes 302 (FIG. 3) and conditioning and digitizing the neural signals with circuitry 304, A/D converter 306, and FIFO 308 (FIG. 3). In addition, the digitized neural signals can be transmitted to host computer 314 (FIG. 3) via telemetry link 310 (FIG. 3) and stored in memory 316 (FIG. 3).

Step 402 can also include collecting output target data (designated M for equations provided herein) from a task generator (not shown). Output data M can include features such as joint angular velocity, EMG amplitude, 3-dimentional hand position or velocity in external or body-centric coordinates, or 3-dimensional hand velocity. Alternatively, any suitable type of output data indicating the efforts of the subject to control an actuator can be recorded for comparison to neural output/activity resulting from the subject attempting to control the actuator. Further, for research purposes, the limb position of the subject (e.g., arm or leg position of the subject) can be recorded for comparison to the neural data collected when the subject is attempting to move the limb.

According to one embodiment, the task generator can train or calibrate host computer 314 before full autonomous use. During this time, a motor task simulator can be presented to a subject. Next, a target (such as a computer-animated object on a display) can move according to a computer process. The subject can attempt to move a cursor using brain control to track the object. In this case, the subject can be used to train or calibrate host computer 314.

As data is collected in step 402, host computer 314 can calculate the criterion variable value (CW) on each neural channel (step 404). The CW can be calculated for predetermined time segments for PC weights or variance. CVV calculations can include computing the principle components of the population neural signal activity and variance on the activity of each channel $$\left( \text{spike counts} = \frac{1}{N} \sum (n_i - n)^2 \right)$$

(designated herein as M) collected from actuator 318. In addition, the neural channels can be ranked by CVV and stored in memory 316 (step 406).

Concurrently, with steps 404 and 406, host computer 314 can calculate the total mutual information between a measured actuator output M and the total neural channel population activity or control data intended for actuator 318 (step 408). In general, the neural population activity P and the actuator output data M is n-dimensional. For example, M can equal the EMG amplitude from n muscles or joint angular velocity at n different joints, and P can represent the activity of n neural channels.

The channel selection process can optimize information obtained about output data M from the neural population activity P. In one embodiment, Shannon mutual information is the primary quantity of interest for optimizing information obtained about output data M. Shannon mutual information is defined by the equation below, which shows the mutual information between two signals M and P, where H is the entropy of a stochastic signal.

$$I(P, M) = H(P) - \langle H(P|M) \rangle$$

$$= \int_M \int_P \rho(m, p) \log_2\left(\frac{\rho(p, m)}{\rho(p)\rho(m)}\right) dP dM$$

Mutual information can be calculated by computing the maximum likelihood estimates of entropies, $H_{ML}$, such that the raw estimate of information, $I_{ML}$, is given by the equation below.

$$I_{ML}(P, M) = \sum_M \sum_P \rho_{emp}(p, m) \log_2\left(\frac{\rho_{emp}(p|M=m)}{\rho_{emp}(p)}\right)$$

In the above equation, $p_{emp}$ is the empirical measure of the probability, given by the equation below for $p_{emp}$. To calculate $p_{emp}$ of a variable X, the sample space of X is first quantized into q levels and the frequency of each quantized value x tabulated to calculate the empirical probability of X taking on the value x. An equation for determining $p_{emp}$ follows:

$$\rho_{emp}(X = x) = \frac{1}{N} \sum_{i=1}^{N} \sum_{j=1}^{k} \delta(t_i - \tau_j)$$

In the above equation, N equals the number of samples, $\delta(t)$ is the Kronecker delta function, and $\{\tau_j\}$ denotes the k occurrences of the variable X taking on the value x. A co-occurrence matrix is constructed from the frequency of joint occurrences of $\{m,p\}$ to calculate $I_{naive}(P,M)$, as provided in the equation above for $I_{ML}$.

Alternative implementations for information include the best upper bounds (BUB) estimate (developed by Liam Paninski) for both total and conditional entropies, and the Strong estimate. The BUB estimate ($\hat{H}_{BUB}$) is provided by the following equation.

$$\hat{H}_{BUB} = \sum_{j=0}^{N} a_{j,N} h_j$$

$$h_j = \sum_{i=1}^{q} (N p_{N,i} == j)$$

In the above equation, == denotes a logical test of equality and $a_{j,N}$ can be selected to minimize $$\sup_x \left( q \left| H(x) - \sum_j a_{j,N} B_{j,N}(x) \right| \right).$$

In the Strong method, many trials of the same time-varying motor task can be performed. The spike trains can be time-aligned and segmented into words of varying length $T_{word}$ ranging from 5 milliseconds to 75 milliseconds. The maximum likelihood entropy rates are computed at the varying word lengths for all the data, and for data at each time bin across trials. Both the total entropy rate and the noise, or conditional, entropy rate can be extrapolated using a least squares regression fit to find $\overline{H}_0\overline{H}(T_{word} \to \infty)$ and $\overline{H}_{n0}=\overline{H}_n(T_{word} \to \infty)$. The difference in these extrapolated points gives the Strong information rate estimate.

Referring again to FIG. 4, the calculated mutual information for the total population $I_{max}$ can be stored in memory 316 (step 410). Alternative to the concurrent implementation of steps 404 and 406 with steps 408 and 410, the steps can be carried out at different times. The total population $I_{max}$ and the rank order of each neural unit can be calculated and stored in memory before the PEA search process begins. The sequence of steps 404/406 and 408/410 can vary based on the particular implementation.

Referring to step 412, host computer 314 implements a process by which the primary encoding subassembly (PEA) is identified. In other words, the PEA is the set of neural channels which most efficiently encodes most of the channel population information. In one embodiment, the PEA process identifies the smallest group of neural channels that encodes 90% of the total channel population information. Alternatively, the PEA process can identify the smallest group of neural channels that encodes 80%-98% of the total channel population information or another suitable percentage.

Next, the identified channel IDs from step 412 can be transmitted via host computer 314 to CPLD 312 (step 414). CPLD 312 can then enable the identified neural channels via control lines 318 and 320 to circuitry 304 and A/D converter 306, respectively. By only enabling the identified neural channels, the transmission of neural signal data between telemetry link 310 and host computer 314 is reduced, and the processing load for FIFO 308 and host computer 314 is reduced.

Host computer 214 can perform PEA identification steps 402-412 a predetermined number of times. According to one embodiment, step 416 includes determining whether the PEA identification steps have been performed twenty (20) times. The first session of steps 402-412 performed by host computer 314 is referred to as a training session.

Next, the PEA identified from the training session can be analyzed for stability (step 418) and determine whether the selected neural channels are stable (step 420). If the selected neural channels are determined to be stable, system 300 can enter a pre-set channel selection mode (step 422).

As noted above, step 420 includes determining whether the selected neural channels are stable. The consistency with which a neural channel is extracted into the PEA is quantified by calculating the frequency with which that neural channel is included in the PEA and comparing it to the expected frequency of a neural channel being included by chance. The proportion of the total number of time segments for which the PEA is defined can be considered equal to the proportion of the total population size that is included in the PEA. The chance frequency is defined as $$\overline{f}_{j,0} = \frac{n_{PEA}}{n} T,$$

where T is the number of time segments used, $n_{PEA}$ is the number of channels in the PEA, and n is the total number of channels. The $\chi^2$ statistic, adjusted by the Yates correction for continuity, can be calculated according to the equation below for those channels whose frequency $f_j$ exceeded $f_0$ to test significance of $f_j$ as an indicator of the stability of inclusion in the PEA.

$$\chi(f_j) = \frac{(f_j - \bar{f}_{j,0} - 0.5)^2}{\bar{f}_{j,0}} + \frac{(\bar{f}_{j,0} = f_j - 0.5)^2}{(T - \bar{f}_{j,0})}$$

The probability with which a channel is considered a unit in the PEA is provided by the proportion of time segments used in which channels with statistically significant frequencies of inclusion are included in the PEA, and is provided by the following equation:

$$\kappa = <f_j^*>_{j*}/T$$

In the above equation, $j^*$ is the identifier of channels whose frequency of inclusion is significantly greater than $f_0$. In the pre-set channel mode, the neural channels with a stability measure above a number $\kappa$ are found, and once identified, the neural channels remain stored as the selected PEA neural channels for enablement by CPLD 312. According to one embodiment, the predetermined number $\kappa$ is 0.5 but can alternatively be another suitable value. Otherwise, if the selected neural channels are determined to be unstable, system 300 can enter a continuous update mode (step 424).

III. C. Channel Selection Modes

As noted above, the channel selection can operate in two modes: (1) continuous update mode; and (2) pre-set channel selection mode. During the first twenty minutes, the device operates in continuous update mode and the appropriate neural channels are enabled according to the PEA identification output, which is continually being recalculated. Meanwhile, the mode for the remainder of the operating session is determined based on stability of the PEAs determined during that training period. The end of an operating session can be the time when the device is turned off or reset.

Figure 5:
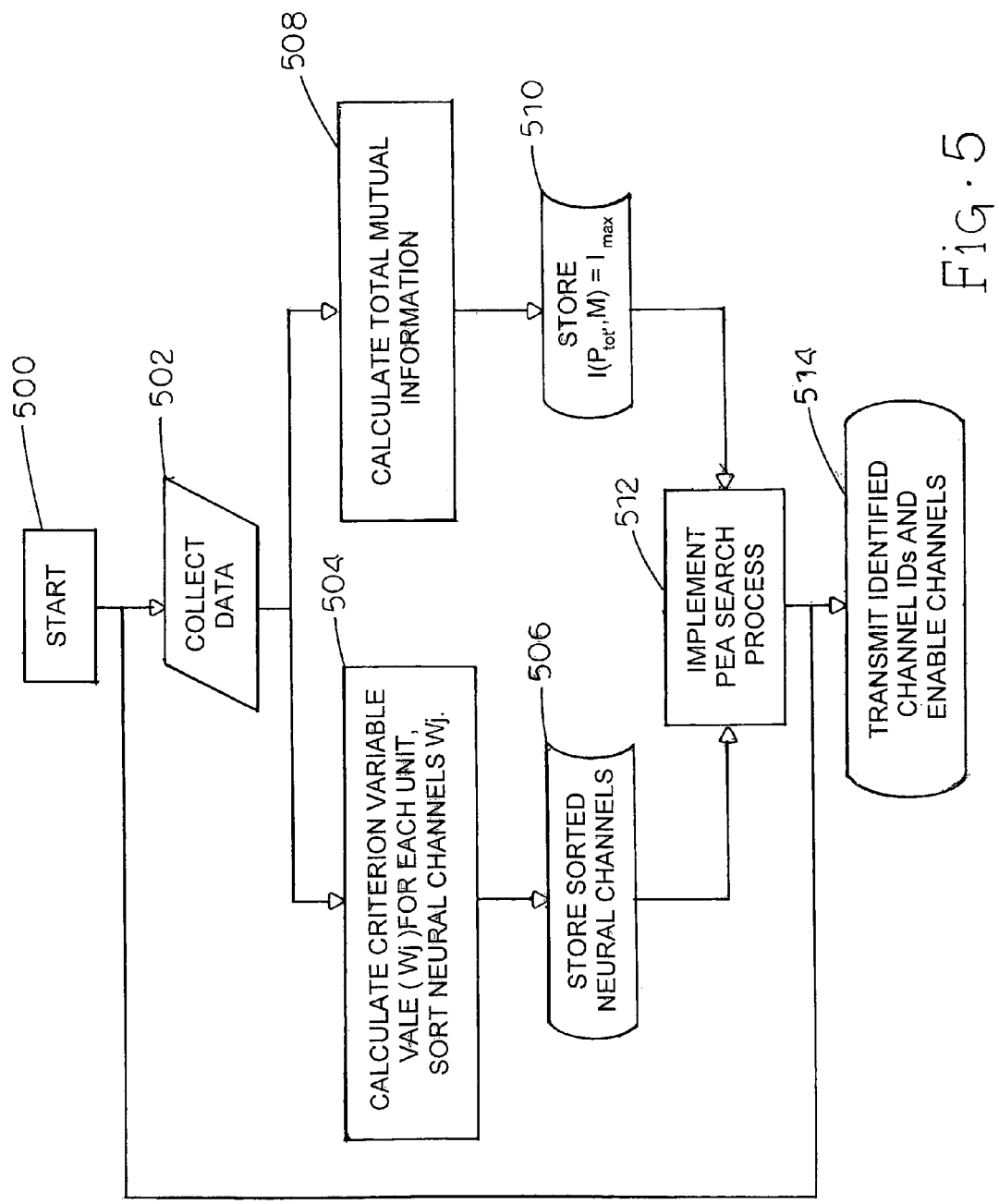
FIG. 5 is a flow chart illustrating an exemplary process for operation in a continuous update mode.

In the continuous update mode, a process is run for monitoring the channels to determine whether any of the currently enabled channels should be disabled or currently disabled should be enabled. FIG. 5 is a flow chart illustrating an exemplary process for operation in a continuous update mode. For example, the flow chart shows steps that can be implemented when system 300 (FIG. 3) enters the continuous update mode (step 424 shown in FIG. 4). Referring to FIG. 5, the process can start at step 500. Next, the process implements steps 502-514 which are similar to steps 402-414 of FIG. 4. Step 502 can collect neural signals on channels and output data from actuator 318 (FIG. 3). The data can be collected for two (2) minutes or another suitable time period. Neural signal collection can include detecting the neural signals with microelectrodes 302 (FIG. 3) and conditioning and digitizing the neural signals with circuitry 304, A/D converter 306, and FIFO 308. In addition, the digitized neural signals can be transmitted to host computer 314 via telemetry link 310 and stored in memory 316. According to one embodiment, the continuous update mode returns to step 502 periodically (e.g., once every 10 minutes).

As data is collected in step 502, host computer 314 can calculate the criterion variable value (CVV) for predetermined time segments of the neural signal on each neural channel (step 504). In addition, the neural channels can be ranked by value and stored in memory 316 (step 506).

Concurrently, with steps 504 and 506, host computer 314 can calculate the mutual information between the actuator output (designated herein as M) and the total neural channel population activity (step 508). The calculated mutual information (designated herein as $I_{max}$) can be stored in memory 316 (step 510). Alternative to the concurrent implementation of steps 504 and 506 with steps 508 and 510, the steps can be carried out at different times. Referring to step 512, host computer 314 implements a process by which the primary encoding subassembly (PEA) is identified.

Next, the identified channel IDs from step 512 can be transmitted via host computer 314 to CPLD 312 (step 514). CPLD 312 can then enable the identified neural channels via control lines 318 and 320 to circuitry 304 and A/D converter 306, respectively. By only enabling the identified neural channels, the transmission of neural signal data between telemetry link 310 and host computer 314 is reduced, and the processing load for FIFO 308 and host computer 314 is reduced.

III. D. Determining PEA

Figure 6:
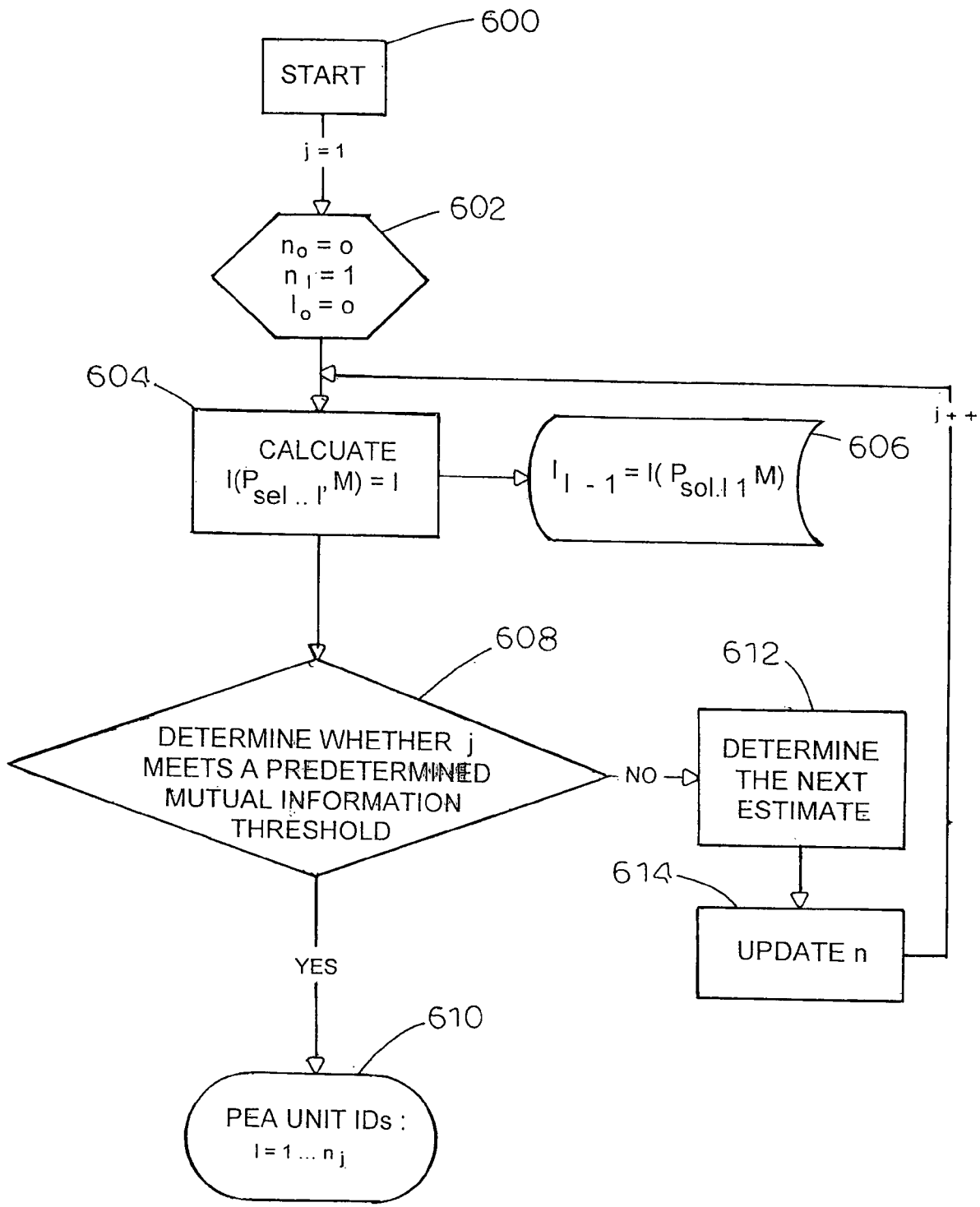
FIG. 6 is a flow chart illustrating an exemplary process for determining the PEA via a Newton method.

FIG. 6 is a flow chart illustrating an exemplary process for determining the PEA via a Newton method. This exemplary process can be used by host computer 314 (FIG. 3) in the PEA search process of steps 412 and 512 of FIGS. 4 and 5, respectively, for determining PEA. The process can identify the smallest group of neurons that encodes a predetermined threshold (e.g., 90%). Generally, the neural channels are ordered in descending order by CVV, and the rank ordering is stored in memory. The number of neural channels (n) to be included in the PEA can be determined by searching iteratively along the information versus sub-population size $I(P_{self}, M)$ curve.

Referring to FIG. 6, the process can start at step 600. At step 602, initial values for the process are set before implementing an iterative search along the information versus sub-population size $(I(P_{self}, M)$ curve. In one embodiment, the first estimate of required number of channels to reach the predetermined mutual information threshold no is initialized to 0, the second estimate of n, $n_1$, is initialized to 1, and mutual information lo is set to 0. At each iteration of the process, $n_j$ can be updated, while information is calculated for those $n_j$ neural channels.

At step 604, mutual information $I_j$ can be determined for the current iteration j. At step 606, as noted above memory 316 (FIG. 3) can store neural channels that are rank ordered by CVV. This ordering by CVV can occur, for example, in steps 404 and 504 of FIGS. 4 and 5, respectively. Next, at step 606, the mutual information $I_j$ current iteration is stored for comparison to the mutual information $I_{j+1}$ determined in the next iteration.

At step 608, the process determines whether the new estimate of mutual information meets a predetermined mutual information threshold. According to one embodiment, this can be determined based on the following equation, wherein $I_{max}$ is maximum mutual information for the total channel population:

$$0.90 < I_j/I_{max}$$

If the above equation is true, the process proceeds to step 610. At step 610, the identified PEA channels are the first $n_j$ channels by rank order of CVV. Otherwise, the process proceeds to step 612 for another iteration.

Next, the number of channels added on the $j^{th}$ iteration can be determined in steps 612 and 614. At step 612, the next estimate $n_{j+1}$ can be identified by determining the point of intersection between a line connecting two currently known points (i.e., $I_{j-1}$ and $I_j$) and threshold. The two points known on the curve are one of the points from the previous iteration (mutual information $I_{j-1}$ from step 606) and the newly computed mutual information at the new estimate $(I_j)$ According to one embodiment, the next estimate can be determined with the following equations (where j=1, 2, . . . $P_{sel,j}$ is the subassembly of units selected by the criterion on the $j^{th}$ iteration, $n_o=0$, $n_1=1$, and $I(P_{sel,0}, M)=0$):

$$\Delta_j = \frac{I(P_{sel,j}, M) - I(P_{sel,j-1}, M)}{n_j - n_{j-1}}$$

Next, at step 614, the next estimate $n_{j+1}$ can be updated with the following equation:

$$n_{j+1} = n_j + \frac{0.90 I_{max} - I(P_{sel,j}, M)}{\Delta_j}$$

The process can continue to step 604 for another iteration.

The selection methods, systems, and computer program products described herein can be useful for improving the efficiency of neural data systems. In addition, the subject matter described herein can provide an improved method for studying the importance of individual neural channels in neural population encoding. The results of these studies can direct electrode implantation procedures to target areas found to contain most frequently extracted into the PEA.

It will be understood that various details of the subject matter disclosed herein may be changed without departing from the scope of the subject. Furthermore, the foregoing description is for the purpose of illustration only, and not for the purpose of limitation.

What is claimed is:

1. A method for neural channel selection in a multi-channel system, the method comprising:
   (a) receiving a plurality of neural signals on a first plurality of channels;
   (b) calculating criterion variable value for the neural signal on each of the channels;
   (c) ranking the channels by the criterion variable value;
   (d) calculating mutual information between a measured output and a total population activity for the first plurality of channels; and
   (e) determining a second plurality of channels that encodes a predetermined amount of the mutual information, wherein the second plurality of channels is a subset of the first plurality of channels.

2. The method according to claim 1, wherein receiving the plurality of neural signals comprises receiving the neural signals from a plurality of neural sensors for detecting the neural signals from neurons.

3. The method according to claim 1, wherein receiving the plurality of neural signals comprises conditioning the neural signals.

4. The method according to claim 1, wherein calculating criterion variable value comprises calculating criterion variable value for between about 2 minutes and 10 minutes.

5. The method according to claim 1, wherein calculating criterion variable value comprises determining principle components of neural signal activity of the first plurality of channels.

6. The method according to claim 5, wherein calculating criterion variable value comprises determining variance of the neural signal activity of each channel of the first plurality of channels.

7. The method according to claim 1, wherein calculating mutual information comprises determining Shannon mutual information.

8. The method according to claim 7, wherein the Shannon mutual information is defined by the following equation:

$$I(P, M) = H(P) - \langle H(P|M) \rangle$$
$$= \int_M \int_P p(m, p) \log_2 \left( \frac{p(p, m)}{p(p)p(m)} \right) dP dM$$

where M is the measured output, P is the control data, and H is the entropy of a stochastic signal.

9. The method according to claim 8, comprising determining maximum likelihood estimates of entropies, wherein a raw estimate of information is provided by the following equation:

$$I_{ML}(P; M) = \sum_M \sum_P p_{emp}(p, m) \log_2 \left( \frac{p_{emp}(p|M=m)}{p_{emp}(p)} \right)$$

wherein $p_{emp}$ is the empirical measure of the probability, given by the following equation:

$$p_{emp}(X = x) = \frac{1}{N} \sum_{i=1}^{N} \sum_{j=1}^{k} \delta(t_i - \tau_j)$$

wherein $\delta(t)$ is the Kronecker delta function, and $\{\tau_j\}$ is the k occurrences of the variable X taking on the value x.

10. The method according to claim 1, wherein calculating mutual information comprises determining a best upper bounds estimate.

11. The method according to claim 1, wherein calculating mutual information comprises utilizing a Strong method.

12. The method according to claim 1, wherein the predetermined amount is greater than about 90%.

13. The method according to claim 1, wherein determining the second plurality of channels comprises searching the ranked channels for the channels that encode the predetermined amount of the mutual information.

14. The method according to claim 1, comprising determining whether the second plurality of channels are stable.

15. The method according to claim 1, comprising selectively enabling or disabling channels from among the first plurality of channels such that the first plurality of channels includes the same channels as the second plurality of channels.

16. The method according to claim 1, comprising selectively conditioning only the neural signals on the second plurality of channels from among the first plurality of channels.

17. The method according to claim 1, comprising selectively transmitting only the neural signals on the second plurality of channels from among the first plurality of channels.

18. The method according to claim 17, comprising providing a controller for receiving neural signals on the second plurality of channels.

19. The method according to claim 18, comprising operating the controller to transmit control signals for controlling the actuator, wherein the control signals are based on the received neural signals on the second plurality of channels.

20. A system for neural channel selection in a multi-channel system, the system comprising:
(a) a signal receiver for receiving a plurality of neural signals on a first plurality of channels; and
(b) a controller operable for the following operations:
(i) calculate criterion variable value for the neural signal on each of the channels;
(ii) rank the channels by the criterion variable value;
(iii) calculate mutual information between a measured output and a total population activity for the first plurality of channels; and
(iv) determining a second plurality of channels that encodes a predetermined amount of the mutual information, wherein the second plurality of channels is a subset of the first plurality of channels.

21. The system according to claim 20, wherein the signal receiver is operable to receive the neural signals from a plurality of neural sensors for detecting the neural signals from neurons.

22. The system according to claim 20, wherein the signal receiver is operable to condition the neural signals.

23. The system according to claim 20, wherein the controller is operable to calculate criterion variable value for between about 2 minutes and 10 minutes.

24. The system according to claim 20, wherein the controller is operable to determine principle components of neural signal activity of the first plurality of channels.

25. The system according to claim 24, wherein the controller is operable to determine the variance of the neural signal activity of each channel of the first plurality of channels.

26. The system according to claim 20, wherein the controller is operable to determine Shannon mutual information.

27. The system according to claim 26, wherein the Shannon mutual information is defined by the following equation:

$$I(P, M) = H(P) - \langle H(P|M) \rangle$$
$$= \int_M \int_P p(m, p) \log_2\left(\frac{p(p, m)}{p(p)p(m)}\right) dP dM$$

where M is the measured output, P is the control data, and H is the entropy of a stochastic signal.

28. The system according to claim 27, wherein the controller is operable to maximum likelihood estimates of entropies, wherein a raw estimate of information is provided by the following equation:

$$I_{ML}(P; M) = \sum_M \sum_P p_{emp}(p, m) \log_2\left(\frac{p_{emp}(p|M=m)}{p_{emp}(p)}\right)$$

wherein $p_{emp}$ is the empirical measure of the probability, given by the following equation:

$$p_{emp}(X = x) = \frac{1}{N} \sum_{i=1}^{N} \sum_{j=1}^{k} \delta(t_i - \tau_j)$$

wherein $\delta(t)$ is the Kronecker delta function, and $\{\tau_j\}$ is the k occurrences of the variable X taking on the value x.

29. The system according to claim 20, wherein the controller is operable to determine a best upper bounds estimate to calculate mutual information.

30. The system according to claim 20, wherein the controller is operable to utilize a Strong method to calculate mutual information.

31. The system according to claim 20, wherein the predetermined amount is greater than about 90%.

32. The system according to claim 20, wherein the controller is operable to search the ranked channels for the channels that encode the predetermined amount of the mutual information.

33. The system according to claim 20, wherein the controller is operable to determine whether the second plurality of channels are stable.

34. The system according to claim 20, wherein the controller is operable to selectively enable or disable channels from among the first plurality of channels such that the first plurality of channels includes the same channels as the second plurality of channels.

35. The system according to claim 20, wherein the controller is operable to selectively condition only the neural signals on the second plurality of channels from among the first plurality of channels.

36. The system according to claim 20, wherein the controller is operable to selectively transmit only the neural signals on the second plurality of channels from among the first plurality of channels.

37. The system according to claim 36, comprising a controller for receiving neural signals on the second plurality of channels.

38. The system according to claim 37, wherein the controller is operable to transmit control signals for controlling the actuator, wherein the control signals are based on the received neural signals on the second plurality of channels.

39. A computer program product comprising computer-executable instructions embodied in a computer-readable medium for performing steps comprising:
(a) receiving a plurality of neural signals on a first plurality of channels;
(b) calculating criterion variable value for the neural signal on each of the channels;
(c) ranking the channels by the criterion variable value;
(d) calculating mutual information between a measured output and a total population activity for the first plurality of channels; and
(e) determining a second plurality of channels that encodes a predetermined amount of the mutual information, wherein the second plurality of channels is a subset of the first plurality of channels.

40. The computer program product according to claim 39, wherein receiving the plurality of neural signals comprises receiving the neural signals from a plurality of neural sensors for detecting the neural signals from neurons.

41. The computer program product according to claim 39, wherein receiving the plurality of neural signals comprises conditioning the neural signals.

42. The computer program product according to claim 39, wherein calculating criterion variable value comprises calculating criterion variable value for between about 2 minutes and 10 minutes.

43. The computer program product according to claim 39, wherein calculating criterion variable value comprises determining principle components of neural signal activity of the first plurality of channels.

44. The computer program product according to claim 43, wherein calculating criterion variable value comprises determining variance of the neural signal activity of each channel of the first plurality of channels.

45. The computer program product according to claim 39, wherein calculating mutual information comprises determining Shannon mutual information.

46. The computer program product according to claim 45, wherein the Shannon mutual information is defined by the following equation:

$$I(P, M) = H(P) - \langle H(P|M) \rangle$$
$$= \int_M \int_P p(m, p) \log_2 \left( \frac{p(p, m)}{p(p)p(m)} \right) dP dM$$

where M is the measured output, P is the control data, and H is the entropy of a stochastic signal.

47. The computer program product according to claim 46, comprising determining maximum likelihood estimates of entropies, wherein a raw estimate of information is provided by the following equation:

$$I_{ML}(P, M) = \sum_M \sum_P p_{emp}(p, m) \log_2 \left( \frac{p_{emp}(p|M=m)}{p_{emp}(p)} \right)$$

wherein $p_{emp}$ is the empirical measure of the probability, given by the following equation:

$$p_{emp}(X = x) = \frac{1}{N} \sum_{i=1}^{N} \sum_{j=1}^{k} \delta(t_i - \tau_j)$$

wherein $\delta(t)$ is the Kronecker delta function, and $\{\tau_j\}$ is the k occurrences of the variable X taking on the value x.

48. The computer program product according to claim 39, wherein calculating mutual information comprises determining a best upper bounds estimate.

49. The computer program product according to claim 39, wherein calculating mutual information comprises utilizing a Strong method.

50. The computer program product according to claim 39, wherein the predetermined amount is greater than about 90%.

51. The computer program product according to claim 39, wherein determining the second plurality of channels comprises searching the ranked channels for the channels that encode the predetermined amount of the mutual information.

52. The computer program product according to claim 39, comprising determining whether the second plurality of channels are stable.

53. The computer program product according to claim 39, comprising selectively enabling or disabling channels from among the first plurality of channels such that the first plurality of channels includes the same channels as the second plurality of channels.

54. The computer program product according to claim 39, comprising selectively conditioning only the neural signals on the second plurality of channels from among the first plurality of channels.

55. The computer program product according to claim 39, comprising selectively transmitting only the neural signals on the second plurality of channels from among the first plurality of channels.

56. The computer program product according to claim 55, comprising providing a controller for receiving neural signals on the second plurality of channels.

57. The computer program product according to claim 56, comprising operating the controller to transmit control signals for controlling the actuator, wherein the control signals are based on the received neural signals on the second plurality of channels.

* * * * *